United States Patent [19]
Liberti et al.

[11] Patent Number: 5,186,827
[45] Date of Patent: Feb. 16, 1993

[54] APPARATUS FOR MAGNETIC SEPARATION FEATURING EXTERNAL MAGNETIC MEANS

[75] Inventors: Paul A. Liberti, Churchville; Brian P. Feeley, Easton; Dhanesh I. Gohel, Philadelphia, all of Pa.

[73] Assignee: Immunicon Corporation, Huntington Valley, Pa.

[21] Appl. No.: 674,678

[22] Filed: Mar. 25, 1991

[51] Int. Cl.$^5$ .............................................. B01D 35/06
[52] U.S. Cl. .................................... 210/222; 210/223; 422/101
[58] Field of Search ........................ 210/222, 695, 223; 209/224, 228, 232; 435/2; 436/177, 526; 422/101; 335/306

[56] References Cited

U.S. PATENT DOCUMENTS

| | | | |
|---|---|---|---|
| 564,858 | 7/1896 | Whitacre et al. | 209/232 |
| 3,402,820 | 9/1968 | Lohmann | 210/222 |
| 3,567,026 | 3/1971 | Kolm | 210/222 |
| 3,676,337 | 7/1972 | Kolm | 210/222 |
| 3,902,994 | 9/1975 | Maxwell et al. | 209/214 |
| 3,970,518 | 7/1976 | Giaever | 195/1.5 |
| 3,985,649 | 10/1976 | Eddelman | 210/695 |
| 4,018,886 | 4/1977 | Giaever | 424/12 |
| 4,141,687 | 2/1979 | Forrest et al. | 23/230 R |
| 4,209,394 | 6/1980 | Kelland | 210/222 |
| 4,230,685 | 10/1980 | Senyei et al. | 424/12 |
| 4,267,234 | 5/1981 | Rembaum | 428/403 |
| 4,452,773 | 6/1984 | Molday | 424/1.1 |
| 4,498,987 | 2/1985 | Inaba | 209/224 |
| 4,554,088 | 11/1985 | Whitehead et al. | 252/62.54 |
| 4,659,678 | 4/1987 | Forrest et al. | 436/512 |
| 4,663,029 | 5/1987 | Kelland et al. | 209/214 |
| 4,795,698 | 1/1989 | Owen et al. | 435/4 |
| 4,895,650 | 1/1990 | Wang | 210/222 |

OTHER PUBLICATIONS

*Immunoassays for Clinical Chemistry*, pp. 147-162, Hunter et al. editors.
*The Properties of Magnetic Supports in Relation to Immobilized Enzyme Reactors*, Robinson et al., Biotechnology and Bioengineering, vol. XV (1973).
The Dynal MPC-1 (manufactured by Dynal, Inc., Great Neck, N.Y.)–product information sheet (1987).
BioMag Separator (manufactured by Advanced Magnetics, Inc., Cambridge, Mass.)–catalog pages (3 sheets).
Magnetic separator (manufactured by Ciba-Corning Medical Diagnostics, Wampole, Mass.)–catalog cover and catalog pages (2 sheets).
Magnetic Separator System (manufactured by Serono Diagnostics, Norwell, Mass.)–catalog pages (2 sheets).
Magnetic separator (made by Miltery Biotech GmbH, Gladbach, Germany)–product information literature.
High Gradient Magnetic Separation Theory and Applications, R. R. Oder, IEEE Transactions on Magnetics, vol. MAG-12, No. 5, Sep. 1976.
Magnetite-Protein Conjugates for the Separation of Cells by High Gradient Magnetic Filtration, C. S. Owen et al., Cell Separation Methods and Selected Applications, vol. 4, 1987.
Magnetic Separation Techniques: Their Application to Medicine, J. T. Kemshead et al., Molecular and Cellular Biochemistry 67. 11-18 (1985).
Magnetic Solid-Phase Radioimmunoassy, L. S. Hersh et al., Clinica Chimica Acta, 63 (1975) 69-72.

*Primary Examiner*—Robert A. Dawson
*Assistant Examiner*—Matthew O. Savage
*Attorney, Agent, or Firm*—Dann, Dorfmann, Herrell and Skillman

[57] ABSTRACT

A magnetic separator for separating magnetic particles from a non-magnetic test medium is disclosed herein. The magnetic separator includes a non-magnetic container having a peripheral wall with an internal surface area for receiving the test medium, and magnetic means for generating a magnetic field gradient within the container in which the magetic field is stronger in the test medium along the internal surface area of the peripheral wall than in the medium most distant from the wall.

18 Claims, 2 Drawing Sheets

APPARATUS FOR MAGNETIC SEPARATION FEATURING EXTERNAL MAGNETIC MEANS

FIELD OF THE INVENTION

The present invention is directed to magnetic separation apparatus and methods in which magnetic particles are used for isolating substances of interest from a non-magnetic test medium by means of high gradient magnetic separation (HGMS).

BACKGROUND OF THE INVENTION

The present invention relates to improvements in magnetic separators and methods of separation of magnetic particles from non-magnetic media, having particular utility in various laboratory and clinical procedures involving biospecific affinity reactions. Such reactions are commonly employed in testing biological samples, such as blood or urine, for the determination of a wide range of target substances, especially biological entities such as cells, proteins, nucleic acid sequences, and the like.

As used herein, the term "target substance" refers to any member of a specific binding pair, i.e., a pair of substances or a substance and a structure exhibiting a mutual affinity of interaction and includes such things as cell components, biospecific ligands and receptors. "Ligand" is used herein to refer to substances, such as antigens, haptens and various cell-associated structures, having at least one characteristic determinant or epitope, which are capable of being biospecifically recognized by and bound to a receptor. "Receptor" is used herein to refer to any substance or group of substances having a biospecific binding affinity for a given ligand, to the substantial exclusion of other substances. Among the receptors determinable via biospecific affinity reactions are antibodies (both polyclonal and monoclonal), antibody fragments, enzymes, nucleic acids, Clq and the like. The determination of any member of a biospecific binding pair is dependent upon its selective interaction with the other member of the pair.

Various methods are available for determining the above-mentioned target substances based upon complex formation between the substance of interest and its specific binding partner. Means are provided in each instance whereby the occurrence or degree of target substance/binding partner complex formation is determinable.

In the case of a competitive immunoassay to determine antigen, for example, the antigen of interest in a test sample competes with a known quantity of labelled antigen for a limited quantity of specific antibody binding sites. Thus, after an appropriate reaction period the amount of labelled antigen bound to specific antibody is inversely proportional to the quantity of antigen in the test sample. Competitive assays for antibodies, employing labeled antibodies (typically monoclonal antibodies) rather than labeled antigen, function in an analogous manner. The resulting immune complexes are separated, for example, by immunoabsorption, physico-chemical adsorption or precipitation of either the complexes or unbound antigen. Antibody-bound labeled antigen is then quantified and a standard curve is constructed from known antigen concentrations, from which unknown concentrations of antigen may be determined.

In contrast, immunometric assays for the determination of antigen, commonly known as "sandwich" assays, involve the use of labeled antibodies instead of labelled analyte. In performing an immunometric assay, a sandwich is formed in which the "layers" are: antibody/multivalent (minimally bivalent) antigen/antibody.

The amount of the labeled antibody which is bound for each complete sandwich complex (antibody/antigen/antibody) is directly proportional to the amount of target antigenic substance present in the test sample. Sandwich assays can be performed in multi-step fashion with polyclonal antibodies or in fewer steps when monoclonals directed to independent antigenic determinants are employed.

In both the conventional competitive immunoassay and the immunometric assay just described, quantification of the target substance requires a physical separation of bound from free labeled ligand or labeled receptor.

Bound/free separations may be accomplished gravitationally, e.g. by settling, or, alternatively, by centrifugation of finely divided particles or beads coupled to the target substance. If desired, such particles or beads may be made magnetic to facilitate the bound/free separation step. Magnetic particles are well known in the art, as is their use in immune and other bio-specific affinity reactions. See, for example, U.S. Pat. No. 4,554,088 and *Immunoassays for Clinical Chemistry*. pp. 147-162, Hunter et al. eds., Churchill Livingston, Edinborough (1983). Generally, any material which facilitates magnetic or gravitational separation may be employed for this purpose.

Small magnetic particles have proved to be quite useful in analyses involving biospecific affinity reactions, as they are conveniently coated with biofunctional polymers, e.g., proteins, provide very high surface areas and give reasonable reaction kinetics. Magnetic particles ranging from 0.7-1.5 microns have been described in the patent literature, including, by way of example, U.S. Pat. Nos. 3,970,518; 4,018,886; 4,230,685; 4,267,234; 4,452,773; 4,554,088; and 4,659,678. Certain of these particles are disclosed to be useful solid supports for immunologic reagents, having reasonably good suspension characteristics when mildly agitated. Insofar as is known, however, absent some degree of agitation, all of the magnetic particles presently in commercial use settle in time and must be resuspended prior to use. This adds another step to any process employing such reagents.

Small magnetic particles, such as those mentioned above, generally fall into two broad categories. The first category includes particles that are permanently magnetized; and the second comprises particles that become magnetic only when subjected to a magnetic field. The latter are referred to herein as magnetically responsive particles. Materials displaying magnetically responsive behavior are sometimes described as superparamgnetic. However, certain ferromagnetic materials, e.g., magnetic iron oxide, may be characterized as magnetically responsive when the crystal size is about 300Å or less in diameter. Larger crystals of ferromagnetic materials, by contrast, retain permanent magnet characteristics after exposure to a magnetic field and tend to aggregate thereafter. See P. Robinson et al., *Biotech Bioeng.* XV:603-06 (1973).

Magnetically responsive colloidal magnetite is known. See U.S. Pat. No. 4,795,698 to Owen et al., which relates to polymer-coated, sub-micron size magnetite particles that behave as true colloids.

The magnetic separation apparatus/method used for bound-free separations of target substance-bearing magnetic particles from test media will depend on the nature and particle size of the magnetic particle. Micron size ferromagnetic, i.e., permanently magnetized, particles are readily removed from solution by means of commercially available magnetic separation devices. These devices employ a single relatively inexpensive permanent magnet located external to a container holding the test medium. Examples of such magnetic separators are the MAIA Magnetic Separator manufactured by Serono Diagnostics, Norwell, Mass., the DYNAL MPC-1 manufactured by DYNAL, Inc., Great Neck, N.Y. and the BioMag Separator, manufactured by Advanced Magnetics, Inc., Cambridge, Mass. A specific application of a device of this type in performing magnetic solid-phase radioimmunoassay is described in L. Hersh et al., magnetic separator, manufactured by Ciba-Corning Medical Diagnostics, Wampole, Mass. is provided with rows of bar magnets arranged in parallel and located at the base of the separator. This device accommodates 60 test tubes, with the closed end of each tube fitting into a recess between two of the bar magnets.

An automated continuous-flow radioimmunoassay system employing cellulose-coated magnetic particles is described in U.S. Pat. No. 4,141,687. The automated system exemplified in the '687 patent includes elaborate electromagnetic traps which are operable in a pre-determined sequence by a programmer device under the control of a sample detector.

The above-described magnetic separators have the disadvantage that the magnetic particles attracted toward the magnets tend to form in multiple layers on the inner surface of the sample container where they are entrapped along with impurities that are difficult to remove even with vigorous washing.

Colloidal magnetic materials are not readily separable from solution as such, even with powerful electro-magnets but, instead, require high gradient field separation techniques. See, R. R. Oder, *IEEE Trans. Magnetics*, 12: 428-35 (1976); C. Owen and P. Liberti, *Cell Separation: Methods and Selected Applications*, Vol. 5, Pretlow and Pretlow eds., Academic Press, N.Y., (1986); J. T. Kemshead and J. Ugelstad, *Magnetic Molecular and Cellular Biochem.*, 67, 11-18 (1985). The gradient fields normally used to filter such materials generate hugh magnetic forces. Another useful technique for performing magnetic separations of colloidal magnetic particles from a test medium, by various manipulations of such particles, e.g., addition of agglomerating agents, is the subject of co-pending and commonly owned U.S. patent application Ser. No. 389,697, filed Aug. 4, 1989.

High gradient magnetic separation (HGMS) is typically accomplished by using a device having a separation chamber in which a wad of magnetic stainless steel wire is disposed between the poles of a conventional electro- or superconducting magnet and serves to generate large field gradients around the wire which exert a strong attractive force on target substance-bearing magnetic particles.

A commercially available high gradient magnetic separator of the type described immediately above is the MACS device made by Miltenyi Biotec GmbH, Gladback, West Germany, which employs a column filled with a non-rigid steel wool matrix in cooperation with a permanent magnet. In operation, the enhanced magnetic field gradient produced in the vicinity of the steel wool matrix attracts and retains the magnetic particles while the non-magnetic test medium passes through and is removed from the column. Similar magnetic separators employing a steel wool matrix for separating colloidal size magnetic components from a slurry containing same are also disclosed in U.S. Pat. Nos. 3,567,026, 3,676,337 and 3,902,994. In the last mentioned patent, the separator is provided with a magnetic wool matrix capable of movement into and out of the influence of a magnetic field as a continuously moving element.

It has been found that the steel wool matrix of such prior art HGMS devices often gives rise to non-specific entrapment of biological entities, other than the target substance, which cannot be removed completely without extensive washing and resuspension of the particles bearing the target substance. Moreover, the size of the column in many of the prior art HGMS devices requires substantial quantities of experimental materials, which limits their use in performing various important laboratory-scale separations. In addition, the steel wool matrix may be harmful to certain sensitive cell types.

A useful magnetic separator that avoids problems identified above is the subject of co-pending and commonly owned U.S. patent application Ser. No. 588,662, filed Sep. 26, 1990. The separator of this co-pending application comprises magnetic means featuring a pair of confronting magnets external to the container and a magnetic gradient intensifying means positioned within a container holding the test medium. The magnetic particles adhere to the magnetic means within the container which serves to separate or remove the particles from the test medium.

U.S. Pat. No. 4,663,029 relates to an HGMS device which is stated to be an improvement with respect to devices employing a magnetic wool matrix as the magnetic field gradient intensifier, as well as to devices relying on differences in magnetic susceptibility of particles in a fluid to effect separation. The '029 patent describes an apparatus for continuous magnetic separation of particles from a slurry according to their magnetic moment, by passing the slurry through a separator comprising a non-magnetic canister with a magnetized wire or rod extending adjacent to the canister. The wire is magnetized by a magnetic field to create a magnetization component transverse to the longitudinal axis of the wire, thereby to provide a field gradient extending everywhere within the canister space and exerting a radial force on particles passing through the canister. Depending upon the orientation of the magnetic field relative to the canister, diamagnetic particles in the slurry can be attracted toward the wire and paramagnetic particles repelled, or vice versa, for a magnetic field usually rotated by 90° with respect to the plane of the canister.

From the foregoing review of the prior art, it is apparent that HGMS affords certain advantages in performing medical or biological analyses based on biospecific affinity reactions involving colloidal magnetic particles. Nevertheless, it would be desirable to provide HGMS apparatus and methods which are of relatively simple construction and operation, relying only on gradient intensifying means external to the separation chamber, and yet maximizing magnetic field gradients, and which reduce entrapment of nontarget substances, eliminate loss of immobilized target substance due to shear forces or collisions with other biological entities, and enable use of standard microtiter plate wells, and the like. Such a development would clearly be of practical utility in conducting various laboratory-scale separations, particularly in immunoassays and cell sorting.

SUMMARY OF THE INVENTION

It is an object of this invention to provide magnetic separation apparatus and methods capable of generating a high gradient magnetic field within a non-magnetic test medium to separate magnetically responsive colloidal particles from the test medium. Unlike relatively larger size magnetic particles which tend to settle out of an aqueous medium, magnetically responsive colloidal particles remain suspended in an aqueous medium for an indefinite period, thereby making them readily accessible to target substances.

The magnetic separator of the invention comprises at least one container and magnetic means capable of generating a high gradient magnetic field in the test medium within the container. The container has a peripheral wall with an internal surface area and is adapted to receive the test medium with the magnetically responsive colloidal particles therein (hereinafter "the test medium being separated"). As will be described in further detail below, the magnetic field gradient generating means is disposed outside the container and provides an "open" field gradient inside the container, wherein the magnetic field is stronger in the test medium along the internal wall surface of the container than it is in the test medium most distant from the wall.

If the test medium being separated is in a steady state, e.g., in a batch-type operation, suitable containers include microtiter wells, test tubes, capillary tubes closed at one end, or other nonmagnetic cylindrical walled vessels defining a chamber for performing the desired separation. Furthermore, a plurality of test samples may be processed simultaneously through the use of a carrier capable of holding more than one sample container. In a preferred form, the carrier includes means for holding a plurality of containers around the periphery of the carrier.

If the test medium is to pass continuously through the separator, a suitable container is a conduit or tube having openings at each end. Such containers are preferably non-magnetic, e.g., glass or plastic, and of cylindrical configuration. Preferably, the container has an inlet opening at one end for receiving the test medium which is exposed to the high magnetic field gradient at the center portion of the container. In this particular embodiment, the container may also have one or more non-magnetic baffles spaced apart within the container between the two ends. The baffles are dimensioned to restrict the cross-sectional area of the passageway in which the test medium flows through the container to a region surrounding the axis. The baffles are preferably inclined radially downwardly along the direction of flow, to guide toward the wall any magnetically responsive colloidal particles coming into contact therewith. The conduit preferably has laterally spaced apart outlet means disposed at the end opposite the inlet. One outlet means may be provided along the periphery of the outlet end of the container for collecting the magnetic particles. Another outlet means is centrally positioned at the outlet end for discharging the test medium.

In a particularly preferred embodiment, the magnetic field generating means may comprise sets of four or six permanent magnets or electro-magnets. The magnets are arranged so as to define a cavity which accommodates the container. In this embodiment, the polarity and positioning of the magnets located on the opposite sides of the cavity are such as to produce flux lines which generate a high gradient magnetic field within the test medium in the container. The magnets may be housed in a ferromagnetic yoke, preferably of cylindrical configuration, which serves to enhance the field strength produced by the apparatus. The magnetic field gradient produced by this "multipole" arrangement is characterized by a very strong magnetic field near the edge of the cavity and by virtually no magnetic field at the center of the cavity. Accordingly, magnetic particles in the test medium adjacent the wall of the container near the edge of the cavity are subject to considerably greater magnetic force than particles in the test medium furthest from the wall of the container, toward the center of the cavity where the field strength falls away to zero.

The magnetic means may advantageously comprise magnetic flux concentrating means, particularly, if the cavity defined by the magnets is much larger than the cross-section of the container or carrier. Suitable for this purpose are pole pieces of various geometries, which are magnetized or magnetizable via an induced field. The magnets comprising the magnetic means may be attached magnetically to, or otherwise joined to the yoke, e.g. by cementing with epoxy, to hold the magnets in a fixed position relative to one another.

The physical properties of the magnetic particles preferably used in the practice of this invention, particularly the relatively small particle size, permit a level of operating efficiency which, insofar as is known, has not been achievable heretofore. Furthermore, by controlling the quantity of magnetic particles added to the test medium, relative to the exposed surface area of the wall of the container in contact with the test medium and controlling the orientation of such exposed surface, so as to be substantially coextensive with the flux lines of the magnetic field, it is possible to cause the magnetic particles to adhere along the exposed surface of the container wall in a substantially single layer, corresponding in thickness to about the size of the magnetic particles and any substance or material borne thereby. By operating in this way, occlusion of nonspecifically bound substances in the immobilized magnetic particles is virtually negligible.

In separating magnetically responsive colloidal particles from a non-magnetic test medium in accordance with the methods of the invention, the particles are initially dispersed in the non-magnetic test medium, forming a stable suspension therein. The magnetic particles typically comprise a receptor capable of specific binding to a target substance of interest in the test medium. If it is desired to separate target substances from test medium in a steady state, a suitable container holding the test medium and the receptor-magnetic particle conjugates are placed in the magnetic separator for batch-wise processing. The external magnetic means disposed around the container produces a magnetic field gradient in the test medium, which causes the magnetic particles to move toward the wall and to become adhered thereto.

In the method of the invention which employs a plurality of containers held in a carrier, the magnetic field gradient causes the magnetically responsive colloidal particles in the test medium to move toward and adhere to the wall of each container closest to the magnetic means. In accordance with this method, the orientation of the wall of each container in the carrier relative to the magnetic means may be controllable to cause the particles to adhere more uniformly around the wall of each container.

In another embodiment of the method of the invention, the test medium being separated may be flowed through the separator. The magnetic field gradient intensifying means produces an "open" field gradient of sufficient strength to pull the magnetic particles from the test medium moving at a predetermined rate and to adhere them to the wall. The non-magnetic test medium is discharged from the container at the outlet end. In a related embodiment of this method, in which the container includes one or more baffles, the test medium to be separated is poured into the inlet opening at one end of the conduit. As the test medium moves through the conduit, the magnetic particles in the test medium are attracted by the magnetic means toward the wall of the conduit and thereby comes in contact with the baffles. The baffles are arranged to cause the particles to be carried toward the wall of the separation vessel. The magnetic means may be operable to cause the particles to become adhered to the interior wall of the separation vessel, or to permit particles to move down the wall for collection at one or more outlets provided along the periphery of the wall at the end opposite the inlet. The test medium may be removed at an outlet laterally spaced from the particle outlet(s) in the center portion of the conduit at the end opposite the inlet end.

In carrying out the methods of the invention, the non-magnetic test medium may be removed from the separator while the magnetic particles are retained on the walls of the container and subjected to further processing, as desired. By performing analyses involving biospecific affinity reactions in this way, resuspension of the magnetic particles bearing the target substance is effectively obviated Accordingly, this method substantially reduces the processing time required for, and thus the cost of, bioanalytical testing.

It has also been discovered, in accordance with the present invention, that in performing the separation methods described herein, there is no need to remove certain reagents present in excess in the test medium before addition of a magnetic common capture agent, such as colloidal magnetic goat antimouse Fc particles. This discovery may be used to practical advantage in that obviating removal of unbound labelling monoclonal antibody, for example, not only simplifies separation procedures generally, but particularly enhances cell viability in bioanalytical procedures performed on cells, e.g., cell separations of clinical interest. In this connection, the present invention also provides a method for separating a membrane-containing bioentity, having a characteristic determinant, from a test sample by the steps of: introducing into the test sample a receptor having binding specificity for the determinant, in an amount sufficient to bind the receptor to the determinant and to provide excess receptor in the test sample; introducing into the test sample, in the presence of the excess receptor, a multivalent capture agent which binds to the determinant-bound receptor, thereby to form a bioentity-receptor-capture agent complex, at least one of the determinant-bound receptor and the capture agent having associated therewith colloidal magnetic particles; and separating the complex from the test sample under the influence of a high gradient magnetic field.

From the foregoing summary, it will be appreciated that the present invention provides separation apparatus and methods of relatively simply construction and operation which enable the efficient and effective separation of target substance-bearing magnetic particles from a test medium.

BRIEF DESCRIPTION OF THE DRAWINGS

Like characters of reference designate like parts in those figures of the drawings in which they occur.

DESCRIPTION OF PREFERRED EMBODIMENTS

Preferred embodiments of the present invention and methods will now be described in detail with reference to the drawings.

The magnetic separation apparatus and methods of the present invention have particular utility in various laboratory and clinical procedures involving biospecific affinity reactions. In such procedures, particles are used which are at once magnetically responsive and colloidal (i.e., particles which are superparamagnetic and capable of remaining in suspension in a non-magnetic test medium), and which comprise a receptor capable of binding the substance of interest in the test sample. In the present method, after the receptor binds the target substance, the magnetic separator removes the magnetic particles from the test medium via HGMS.

Such biospecific affinity reactions may be employed in testing biological samples for the determination of a wide range of target substance, representative of which are cells, cell components, cell subpopulations (both eukaryotic and prokaryotic), bacteria, parasites, antigens, specific antibodies, specific biological factors, such as vitamins, viruses and specific nucleic acid sequences, as in the case of gene probe analysis. Thus, the magnetic separation apparatus and methods of the invention may be used to carry out cell separations for the analysis or isolation of cells including, by way of example: T-cells from a T-cell lymphoma cell line; B-cells from a B-cell lymphoma cell line; CD4 positive cells from leukocytes; lymphocytes from leukocytes; tumor cells from normal cells; and stem cells from bone marrow cells.

The methods of the invention may also be used for immunospecific isolation of monocytes, granulocytes and other cell types; removal of rare cells; depletion of natural killer cells; determination of reticulocytes; and assays for neutrophil function, e.g., for determining changes in membrane potential, performing oxidative burst analysis, phagocytosis assays and opsonization studies.

Similarly, the present magnetic separation apparatus and method may be used in bacterial or parasite separation or analysis, including the separation of various bacteria and parasites from fecal matter, urine, sludges, slurries and water (e.g., ground water or streams). The present invention may also be used in separating various bacteria in food products (liquids to solids) sputum and urine.

The preferred magnetic particles for use in carrying out this invention are particles that behave as true colloids. Such particles are characterized by their submicron particle size, which is generally less than about 200 nanometers (nm.) (0.20 microns) and their stability to gravitational separation from solution for extended periods of time. Suitable materials are composed of a crystalline core of superparamagnetic material surrounded by molecules which may be physically absorbed or covalently attached to the magnetic core and which confer stabilizing colloidal properties. The size of the colloidal particles is sufficiently small that they do not contain a complete magnetic domain, and their Brownian energy exceeds their magnetic moment. As a consequence, North Pole, South Pole alignment and subsequent mutual attraction/repulsion of these colloidal magnetic particles does not appear to occur even in moderately strong magnetic fields, which contributes to their solution stability. Accordingly, colloidal magnetic particles are not readily separable from solution as such even with powerful electromagnets, but instead require a relatively high gradient magnetic field to be generated within the test medium in which the particles are suspended in order to achieve separation of the discrete particles.

Magnetic particles having the above-described properties can be prepared as described in U.S. Pat. No. 4,795,698, the entire disclosure of which is incorporated by reference in the present specification, as if set forth herein in full.

For cell separations, the test medium is typically prepared from appropriately prepared body fluids, such as blood, urine, sputum or secretions. It is preferable to add the colloidal magnetic particles to the test medium in a buffer solution. A suitable buffer solution for this purpose comprises a mixture of 5% bovine serum albumin ("BSA") and 95% of a biocompatible phosphate salt solution, optionally including relatively minor amounts of dextrose, sodium chloride and potassium chloride. The buffer solution should be isotonic, with a pH about 7. The protein serves to decrease interactions which tend to interfere with the analysis. The target substance may be added to the test medium before, after or simultaneously with introduction of the magnetic particles. The methods of the invention take advantage of the diffusion controlled solution kinetics of the colloid magnetic particles, which may be further enhanced by the addition of heat to the test medium. The test medium is usually incubated to promote binding between the receptor and any ligand of interest present therein. Incubation is typically conducted at room temperature or at a temperature slightly above the freezing point of the test medium (i.e., 4° C.). Occasionally, incubation can be carried out at 37° C. The period of incubation is normally of relatively short duration (i.e., about 2-15 minutes). The test medium may be agitated or stirred during the incubation period to facilitate contact between the receptor and ligand.

If a small percentage of the buffer solution is replaced by a suitable anionic polyelectrolyte, binding of the receptor to a material other than the target substance in the test medium (i.e., non-specific binding) is noticeably reduced. Satisfactory results have been obtained using a commercial scale inhibitor sold under the name Tamol 850, which is available from Rohm and Haas, Philadelphia, Pa. Tamol 850 is sold as an aqueous solution of polymethacrylic acid, having a molecular weight of 12,000 (weight average), total solids of 29-31%, density of 9.9 lbs./gal. (at 25° C.), a Brookfield viscosity of 125-325 (at 25°) and a spindle/speed of #2 @60. The addition of about 0.1% to about 3% Tamol 850 (on an active basis) to the phosphate buffer will generally be adequate to reduce non-specific binding in the practice of the invention.

In carrying out the method of the invention in which various bioentities are magnetically separated from a test medium containing excess receptor, antibody which binds selectively to the bioentity of interest is generally used as the receptor. Monoclonal antibody is preferably used for this purpose. However, non-antibody receptors, including antigen for antibody-producing cells or antigen processing cells, lectins, such as concanavilin A, soybean agglutinin, wheat germ agglutinin and the like, biotin-labeled reagents or hapten-labeled reagents, may be used, if desired.

The capture agent is a substance capable of binding selectively to the receptor, so as to form a bioentity-receptor-capture agent complex. Suitable capture agents include Protein A or Protein G, where Ig is used as the receptor; avidin, where a biotin-labeled reagent is used as the receptor; and anti-hapten, where a hapten-labeled reagent is used as the o receptor. Either biotin or a hapten may be used to facilitate capture of lectin receptors, e.g., concanavilin A, soybean, agglutinin or wheat germ agglutinin, which bind selectively to membrane-containing bio-entities comprising carbohydrate or glycoprotein components. Hapten/anti-hapten pairs which are suitable for this purpose include dinitrophenol (DNP)/anti-DNP, fluorescein/anti-fluorescein or arsanilic acid/anti-assanilic acid. The capture agent preferably comprises colloidal magnetic particles which enable separation via high gradient magnetic field; however, the receptor may comprise colloidal magnetic particles, if desired.

After binding of the receptor to the substance of interest is allowed to occur, magnetic separation of the colloidal magnetic particles from the test medium is performed using the apparatus and methods of the present invention. The test medium is placed in or passed through a suitable separation vessel for batch-wise or continuous processing, as desired. Magnetic means disposed around the external periphery of the container generate a high gradient magnetic field or flux within the test medium transverse to the walls of the container. The magnetic means comprises a plurality of north magnetic poles and a plurality of south magnetic poles positioned alternatively around the container. In accordance with certain preferred embodiments of the invention, four or six magnets surround the container with equidistant intervals therebetween, so that the magnetic field is substantially uniform along the walls of the container. The high gradient generated in this way causes the magnetic particles to migrate toward the surface of the wall of the container to which the particles adhere, rendering them easily separable from the test medium.

Figure 1:
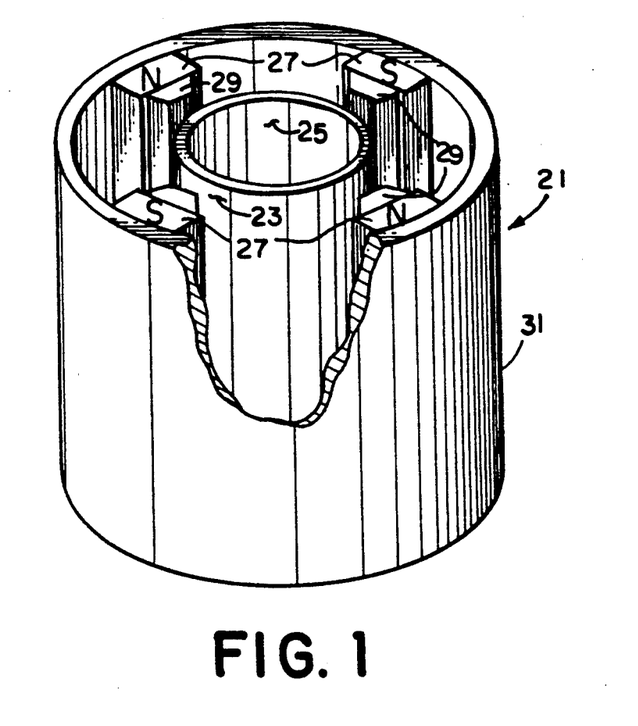
FIG. 1 is a perspective view of a magnetic separation apparatus embodying the present invention, portions of the apparatus being broken away for the purposes of illustration.
Figure 2:
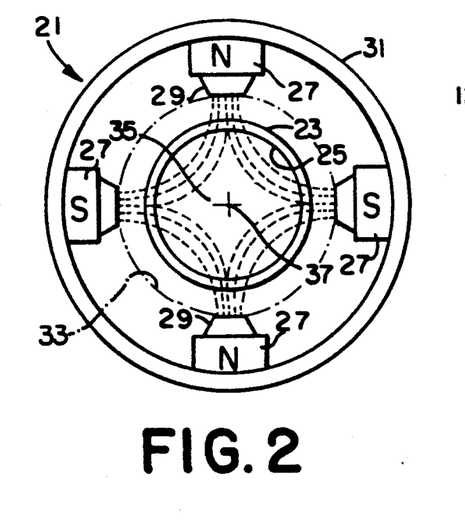
FIG. 2 is a plan view of the apparatus shown in FIG. 1.

FIGS. 1 and 2 illustrate an embodiment of a magnetic separator in accordance with the present invention. The separator 21 comprises a container 23 having a peripheral wall 25 and an open top for receiving the test medium. The magnetic separator also includes four magnets 27 which define a cavity 33 adapted to receive the container. The magnets 27 are equally spaced along the inner surface of cylindrical ferromagnetic housing or yoke 31, on which they are mounted, e.g., by cementing. The magnets may, if desired, be provided with magnetic flux concentrating means, such as pole pieces 29, which permits variation in the lateral dimension of cavity 33 to accommodate containers of different dimensions, or pole pieces which make the field more uniformly radial.

As shown in FIGS. 1 and 2, the container used to hold the test medium is a microtiter well. The container is positioned substantially coaxially with cavity 33 defined by the magnet faces. In that position, the magnetic field in the test medium 35 adjacent to the wall approaches the magnetic field generated by the magnets. In contrast, there is virtually no magnetic field in the part of the container located along the axis 37 of cavity 33, i.e., the test medium most distant from the wall.

The wall of the microtiter well exposed to the test medium provides an ample surface area for adherence of the colloidal magnetic particles. An advantage of the magnetic separator of the invention, when utilized under the conditions described above, is that by appropriately regulating the quantity of magnetic colloid, the particles tend to deposit substantially uniformly upon surfaces in contact with the medium where the magnetic gradient is high. As a result, particles may be caused to be deposited on a broad portion of the internal surface area of the wall in what is effectively a single layer, as opposed to multiple layers or particle agglomerates, which tend to entrap potentially interfering substances, as when formed on a smaller surface, such as occurs in magnetic separators of the prior art. In experiments employing IgG-bearing magnetic colloid, for example, it was found that when colloid mixed with enzyme was collected on the side of a separation vessel, enzyme became trapped as the colloid began to accumulate in layers. In the practice of this invention, by contrast, the colloidal magnetic particles are sufficiently thinly deposited on the container surface that there is virtually no entrapment of potentially interfering substances. To this end, it is preferable that the portion of the container wall surface in contact with the test medium be selected so that the wall's aggregate collecting surface area is greater, by a factor of about 2, than the surface area that wold be occupied by all of the magnetic particles in the test medium, if deposited in a substantially continuous single layer.

For permanent magnet devices, the magnetic field strength of the external magnetic means (magnets 27 in FIG. 2) at the pole faces should be in a range of 4–10 KGauss, and more preferably between about 6–8 KGauss. The preferred distance between each magnet and the container shown in FIGS. 1 and 2 is generally about 0.1 cm. to about 2.0 cm. with the most preferable distance being about 0.5 cm. The field strength of the external magnet or magnets should be great enough, and the distance between the magnets and the container 23 for the test medium short enough to give efficient separation of the magnetic particles. With electromagnets, considerably higher field strengths at the pole faces, on the order of 15–30 KGauss, can be achieved. In this way, very high gradient fields are obtained.

The cavity 33 should be formed by the magnets with sufficient excess space for manipulation of the container 23. For example, an elevating mechanism (now shown) may be positioned in the cavity to raise and support the container 23 in the position illustrated.

The pole pieces 29 illustrated in FIGS. 1 and 2 may be fabricated of any magnetizable material. The pole pieces are shown in the form of magnetized bodies of trapezoidal cross-section, but may be fabricated in other shapes, such as triangular cross-section. These configurations aid in concentrating the magnetic flux emanating from magnets 27. The pole pieces 29 may be held in place on the faces of magnets 27 by magnetic attraction. Alternatively, magnets 27 may be fabricated such that the pole piece is unitary with the body of the magnet.

Figure 3:
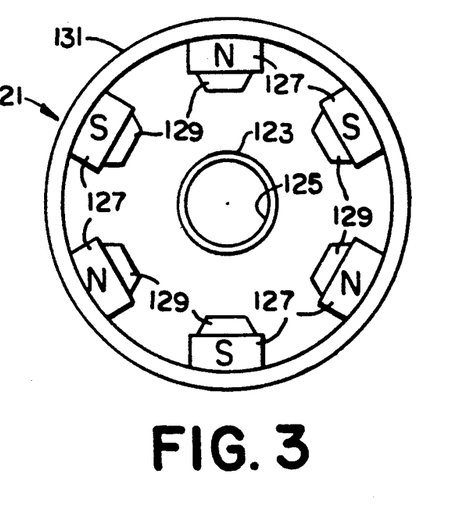
FIG. 3 is a plan view of a related embodiment of the invention having a magnetic means comprising six magnets.

FIG. 3 illustrates another embodiment of the magnetic separator of the invention that is similar to the magnetic separator shown in FIGS. 1 and 2. The separator 121 shown in FIG. 3 comprises a container 123 in the form of a cylindrical tube or the like. The container may be closed at one end, e.g., a test tube for batch-wise processing, or open at both ends, e.g., a capillary or larger diameter tube for continuous processing. The container has a wall 125 and an opening for receiving the test medium being separated. The separator also comprises magnetic means represented by six magnets 127 which are equally spaced around the container.

Figure 4:
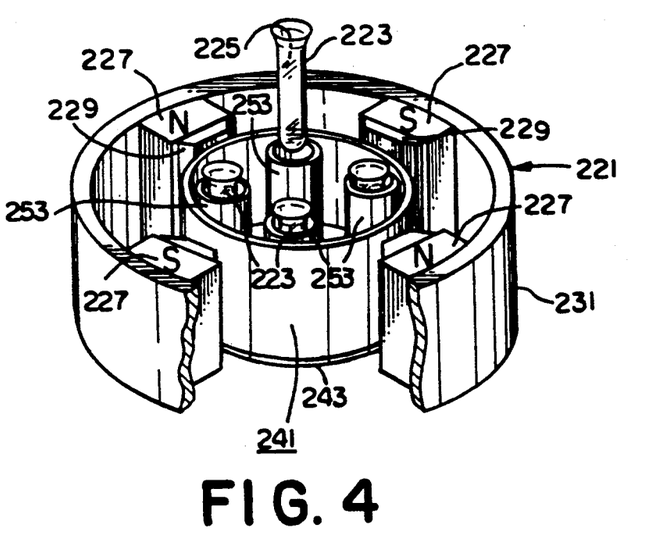
FIG. 4 is a fragmentary perspective view of a related embodiment of the invention in which several containers are held in a carrier.

FIG. 4 illustrates a variation of the magnetic separator of the invention illustrated in FIGS. 1 and 2. In FIG. 4, the separator 221 comprises a plurality of containers 223 held by a carrier 241 and a magnetic means external to the carrier. Each container has a peripheral wall 225 and an open top. The magnetic means comprises four magnets 227 having curved faces disposed concentrically around the carrier.

The carrier 241 comprises a generally planar non-magnetic base 243, with separate non-magnetic compartments 253 fitted into the base at an outer edge thereof. Each such compartment is dimensioned to hold securely one of the containers 223 in an upright position.

Figure 5:
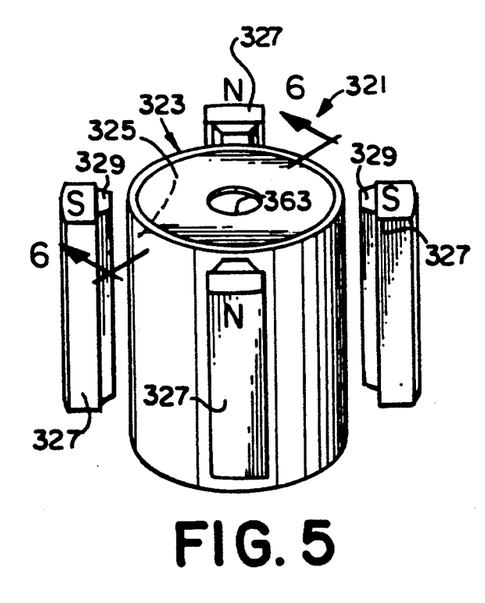
FIG. 5 is a view in perspective of another embodiment of the invention in which a flow-through test container is provided with internal baffles.
Figure 6:
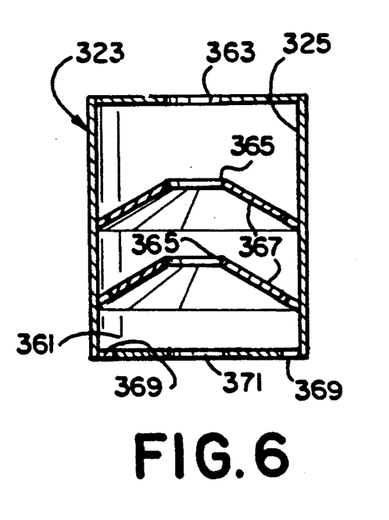
FIG. 6 is a vertical section through the apparatus of FIG. 5.

FIGS. 5 and 6 illustrate another embodiment of the magnetic separator of the invention. The magnetic separator 321 comprises a cylindrical container 323 with openings at either end to permit the test medium being separated to flow through the container. The separator also comprises four magnets 327 which are spaced around the container with substantially equal intervals therebetween.

The container illustrated in FIGS. 5 and 6 has a peripheral wall 325 that defines an inner cross-sectional space 362 inside the container. One end of the container has an inlet port 363 that is dimensioned to permit entry of test medium to the central portion 365 of the inner cross-sectional space between the wall and the central portion. The baffles are also inclined downwardly along the direction of flow toward wall 325. Hence, in passing through the container, the magnetically responsive colloidal particles are attracted by the magnets 327 onto the baffles and toward the wall. The baffles guide the particles along to a point at which the field gradient becomes sufficiently strong to cause the particles to adhere to the wall. The container also has at least two outlets. One outlet 369 is along the periphery of the wall for collection of the particles. A second outlet 371 is aligned with the axis of the container for discharge of the non-magnetic test medium.

The magnetic particles may be separated from the test medium using the magnetic separator apparatus described above, after the test medium has been subjected to the magnetic field for a sufficient time to cause the magnetic particles to migrate and adhere to the container wall. The non-magnetic components of the test media may be removed by decantation or aspiration, with the container still in the separator. A buffer, a wash liquid, or the like may then be added, while the container remains within the separator, to contact the wall for washing the adhering magnetic particles substantially free of any residual non-magnetic components. If desired, the wash liquid may be removed and the process repeated. If it is advantageous to resuspend the magnetic particles, the container may be removed from the magnetic field and manipulated to allow the magnetic particles to be dislodged from the walls and resuspended in a suitable liquid medium, e.g., to facilitate analysis.

The magnetic separation apparatus and methods of the invention permit advantageous use of diffusion controlled solution kinetics of the primary incubation mixture. Moreover, various analytical procedures, including quantitative determinations, may be performed on the magnetically immobilized colloid. Such steps include washes for removal of non-specifically bound substances, secondary immunochemical reactions or detection reactions (e.g., enzymatic, fluorescent or chemiluminescent reactions).

The ability to retain the magnetic particles adhered to the wall of the container after the test medium has been removed is of considerable utility. Certain operations are more efficiently carried out in this way, such as washing or rinsing the target substance, e.g., cells or labeled components of a reaction mixture, while avoiding a separate resuspension step. In addition, secondary reactions such as those involving the interaction of labeled immunoreactive agents with a target substance carried by the magnetic particles may be performed more efficiently with the particles adhered to the wall. Here again, resuspension of the colloidal magnetic particles is avoidable. Furthermore, in performing enzyme-labelled immunoassays in accordance with the present invention, substrate incubation is preferably carried out directly on the colloidal magnetic particles immobilized in the separation apparatus.

Performing the magnetic separation method of the invention batchwise, i.e. in a steady-state system, as described above, instead of in a flow through system, has certain advantages. Immobilized magnetic particles bearing the target substances are not dislodged due to collisions with other particles. Moreover, batchwise operation eliminates dislodgment of immobilized magnetic particles due to shear forces produced by a flowing test medium. In other words, the adherence of the magnetic particles to the wall is sufficiently strong to permit washing, secondary reactions, and interactions with other reagents to occur without appreciable dislodgment of the magnetic particles from the wall. In addition, the adherence of the magnetic particles to the container wall is maintained to some extent even if the container is removed from the magnetic field before further reaction with, or treatment of the particles.

Nevertheless, in certain applications it is very desirable to be able to employ a magnetic separator adapted for use in a flow through process. For example, flow through processes are very desirable for separating large quantities of material of a uniform type. Surprisingly, the separator of the invention avoids the problem of dislodged particles noted above that commonly occurrs when employing a flow through process.

In general, the magnetic particles are relatively easily separated from the container wall after removal from the magnetic field. The particles may be dislodged by contacting the wall with a modified buffer solution, or a bath sonicator. Alternatively, the particles may be collected as they are dislodged from the wall with a probe sonicator.

Multipole magnetic separation devices such as those described above in which near neighbor pole faces are of opposite polarity create high gradient fields wherein the magnitude of the gradient is limited only by the field density at the pole face and the distance separating opposing poles. Compared with gradient fields produced by inducing magnetic fields on ferromagnetic material (fine wires, rods, spheres etc.) placed in external fields, the multipole devices of the invention have substantial advantage because the field strengths at the center of the opposing poles is zero. Hence, the gradients produced are only limited by the ability to produce fields greater than zero.

The following examples further describe in some detail the manner and process of making and using the present invention and set forth the best mode contemplated by the inventors for carrying out the invention, but are not to be construed as limiting the invention. All temperatures given in the examples are in ° C., unless otherwise indicated.

EXAMPLE 1

To demonstrate the utility of high gradient fields produced by multipole apparatus in effecting magnetic separation in accordance with the present invention, quadrupole and hexapole devices were constructed and tested. For this demonstration, permanent rare earth magnets were used (Crumax 355, Crucible Magnetics, Elizabethtown, Ky.); however, electromagnets could also be used, if desired. Quadrupole and hexapole devices similar to those shown FIGS. 1-3 were made comprising a yoke in the form of a 5 cm. long cylindrical steel pipe of 2.5 inch internal diameter (obtainable from plumbing supply distributors) and bar magnets disposed on the inner walls of the cylinder. Crumax 355 bar magnets 1.27 × 1.27 cm. by 5 cm. (magnetized through one of the 1.27 cm. dimensions) were mounted on the inner surfaces of the cylinder, with the long dimension of the bar magnet parallel to the axis of the cylinder. For the quadrupole apparatus, four bar magnets were employed, placed at 90°, 180°, 270° and 360° with respect to a plane normal to the axis of the cylinder. The hexapole apparatus was similarly constructed except that six bar magnets were placed at 60°, 120°, 180°, 240°, 300° and 360° around a cylindrical yoke. In both the quadrupole and hexapole apparatus, the polarity of the magnets alternated around the yoke. For the quadrupole and hexapole apparatus thus constructed, opposing magnet faces were 3.4 cm. apart (pole face gap radius=1.7 cm) and the field density at each pole face measured 5.5 KGauss using a Gauss meter (Applied Magnetics Laboratory, Baltimore, Md.). As the field at the center was 0 the average field gradient was 3.2 KGauss/cm.

To evaluate the effectiveness of the quadrupole and hexapole apparatus for radially separating small magnetic particles or cells to which magnetic particles are bound, the following experiments were done. A bovine serum albumin coated magnetic colloidal (60 nm. diameter particles) was prepared by the method described in Example 1 of Owen et al., U.S. Pat. No. 4,795,698. A small agglomerate (200-300 nm) of this magnetic colloid was formed by the addition of NaCl which causes a partial salting-out of the colloid, as described in co-pending U.S. patent application Ser. No. 389,697, filed Aug. 4, 1989. Such agglomerates have magnetic separation properties similar to cells to which are bound magnetic colloids bearing specific cell surface antibodies. Hence, the preparation was useful for assessing how cells would separate in a multipole high gradient field apparatus. This agglomerate is also useful for evaluating separability of the colloid, but in a more reasonable period of time, as compared with separation of the actual colloid. Using 250 ul aliquots of the above-described agglomerate in single microtiter wells (0.7 cm. i.d.) the local magnetic fields within these multipole devices were determined by placement of the wells at different locations within the field and observing the collection of agglomerate on the wall of the microtiter well after clearing from the test medium (generally 3-5 minutes). From these experiments, it was found that for the quadrupole and hexapole apparatus the field forces are radial and substantially axisymmetric over a radius of about 60-70% of the pole face gap radius. Separations performed at greater radii showed that magnetic agglomerate was not collected on the outer radii of the microtiter wall in a uniform manner, whereas highly uniform radial collection was observed at the lesser radii.

To further substantiate the axisymmetry of collection within the radial regions described immediately above, an open-top cylindrical glass vessel of 2 cm. internal diameter containing the above described magnetic agglomerate was placed in the center of the quadrupole or hexapole devices and separation observed. This was done at several dilutions of the agglomerate so that deposits of magnetic particles on the walls of the vessel could be observed at several densities. In all cases, the deposits on the walls were observed to be substantially uniform. When separation was performed in a vessel placed substantially off-center in the apparatus, non-uniformity of collection was observed on the cylinder wall closest to the pole faces.

To demonstrate that a non-agglomerated colloid would separate similarly, a dextran coated colloid (80 nm diameter), prepared as described in U.S. Pat. 4,452,773 to Molday, was placed in the glass vessel described above and allowed to separate for 10 minutes, by which time a uniform deposit was obtained on the walls of the vessel. It is thus reasonable to expect that colloidal magnetic particles are rapidly separable in apparatus of the type described above, in which the gradient fields are higher than those generated in the present experiment.

Although the magnetic field at the center of the apparatus was measured to be zero, magnetic particles were collected from the center of the vessel. Thus, it appears that the thermal energy of small magnetic particles in combination with mixing due to thermal influences in the solvent are sufficient to cause diffusion to the high gradient region of the vessel. Field uniformity and added axisymmetry can theoretically be achieved by appropriate curvature of the pole faces and magnets used to construct multipole devices. By minimizing the gap between near neighbor magnets further reduction in field irregularities near these regions can be achieved.

EXAMPLE 2

Mammalian cells were separated using the multipole apparatus of Example 1, above. The target substance in this experiment was human T-cells (ATCC Accession No. CCL119 CCRF-CEM) which were maintained in cell culture under conditions available from ATCC. Cells were either labeled with chromium 51 ($CR^{51}$) by the procedure of GGV Klaus, *Lymphocytes, a Practical Approach*, IRL Press Ltd., p. 144 (1987), or they were fluorescently labeled with acridine orange according to a procedure well known in the art. After labeling by either procedure, cells were washed in the usual manner. Cells were resuspended to approximately $3 \times 10^6$ cells/ml in a cell-compatible isotonic phosphate buffered saline solution containing 0.1% sodium azide, pH 7.2, supplemented with 1% (w/v) BSA. A dextran coated colloid (80 nm. diameter) which was made by the Molday procedure, as described in U.S. Pat. No. 4,452,773, and showed very high non-specific binding to cells, was used to magnetically label cells. The final concentration of the colloid was 17 ug iron/ml. of cell suspension.

Fluorescently labeled cells were placed in opentop glass cylindrical vessels of 1.76, 2.38 and 3.17 cm. i.d., respectively. These vessels were placed in the center of the quadrupole or hexapole separation apparatus which were mounted on the stage of an inverted microscope (Zeiss Axiovert 35 M, Thornwood, N.Y.) in such a way that separation in all parts of the vessel was observable via fluorescent microscopy of the cells. For the two smaller diameter radii vessels employed, magnetically induced migration of the cells to the peripheral wall of the vessel was completely uniform. When the 3.17 cm. diameter vessel was used, irregularities of collection were observed on the periphery at locations corresponding to the gaps between near neighbor magnets. Thus, for the quadrupole apparatus there were four regions (90°, 180°, 270° and 360°) where excessive collection of cells occurred; and with the hexapole six such regions were observed. Hence, by selecting a separation vessel of appropriate dimensions for a given separation apparatus, substantially uniform deposition of the magnetic particles on the walls of the vessel may be achieved.

EXAMPLE 3

To determine how efficiently cells can be induced to move radially from the center of a multipole device (where the field is zero), radio-labeled cells were placed in a 2.38 cm. i.d. cylindrical vessel which was then placed at the center of the hexapole device constructed as previously described. Aliquots of the test medium were carefully removed periodically from the center of the vessel and counted for $CR^{51}$, from which depletion of cells from this region was calculated. By three minutes, 30% of the cells were removed from the central region, by seven minutes 77% of the cells were removed and by twelve minutes 86% removal was observed. Thus, even in the case of cells which exhibit essentially no thermally induced motion there is sufficient mixing of cells such that they can be pulled from the very center of such devices. This experiment demonstrates that cells flowing through a cylindrically shaped container placed in a multipole apparatus are removable in an efficient manner. Using appropriate flow parameters and with appropriate baffling a multipole device could be used for continuous removal of cells.

EXAMPLE 4

A quadrupole separation apparatus was constructed from a cylindrical steel yoke having 5.78 and 8.32 cm. inner and outer diameter, respectively, and measuring 5.10 centimeter high, and 4 Crumax 355 permanent bar magnets of dimensions 0.635 × 2.54 × 5.10 cm., magnetized through the 2.54 cm. dimension. The four magnets were placed on the inner surface of the cylinder at 90°, 180°, 270° and 360° and aligned such that the 5.10 cm. dimension of each bar magnet was parallel to the axis of the yoke and the 2.54 cm. dimension was radially aligned. As with the above described quadrupoles, opposing magnet faces were of the same polarity and near neighbor magnets had opposite polarities at their faces. To maintain the bar magnets properly aligned, i.e., at 90° to each other, arcuate spacer elements made of aluminum were machined and fitted into the spaces between bar magnets. This arrangement created a quadrupole having a gap between opposing pole faces of 0.70 cm. Using a Gauss meter, the field at the pole face surface was measured at 5.95 KGauss and zero at the center. Thus, the average field gradient for this assembly was 17 KGauss/cm. To determine how well this separation apparatus removed colloidal sized magnetic particles from solution, a 6 cm. length of glass tubing, 0.30 cm. inner diameter, was inserted into the quadrupole along its axis. This tube was connected to a syrine pump (Harvard Apparatus, Dedham, Ma.) such that test medium could be introduced into the glass tubing positioned upright in the field of the quadrupole and subsequently removed for inspection. Bovine serum albumin-coated colloidal magnetic particles of 80 nm. diameter, made according to Example 1 of Owen et al., U.S. Pat. No. 4,795,698, and suspended in 20 mM phosphate buffer, pH 7.5, were drawn up into the glass tubing, positioned in the magnetic field and separation was allowed to take place. When suspensions of this colloidal material containing from 20–100 ug/ml of iron were subjected to the magnetic field gradient, complete separation occurred in about 6 minutes, as determined by spectrophotometric examination of the solution pumped out of the separation tube.

To determine the distribution of the colloidal material on the inner surface of the separation tube, levels of colloidal material similar to the above were separated, after which the mother liquor was pumped from the tube using the syringe pump and the magnetically deposited material was allowed to dry on the inner surfaces of the tube. Deposited material so dried was thereafter not affected by magnetic gradient. From inspection of these tubes, it was apparent that material is evenly deposited on the inner surfaces of the separation tubes.

EXAMPLE 5

Typically, when cells are immune specifically retrieved by means of labelling with cell-specific monoclonal antibody (MAb), it is customary to incubate cells with MAb, wash out excess MAb and next incubate with a multivalent common capture agent, e.g., second antibody or avidin on a suitable solid support, such as magnetic particles. The purpose of removing excess MAb is to prevent agglutination between non-cell bound MAb and the multivalent common capture agent, and also to preserve binding sites on the common capture agent. To demonstrate the efficiency of external gradient field devices for performing immune specific cell separations, while at the same time obviating removal of excess MAb before the addition of common capture magnetic colloid, the following experiments were done. Affinity purified goat anti-mouse Fc (GAMFc) (Jackson Immunoresearch Lab, West Grove, Pa.) was coated along with bovine serum albumin (BSA) onto colloidal magnetic particles as described in U.S. Pat. No. 4,795,698 for use as the common capture agent. The final concentration of GAMFc and BSA on the colloid were 0.7 mg and 0.05 mg, respectively, per milliliter of final colloid. CEM cells were $Cr^{51}$-labelled and resuspended to a final concentration of $2.5 \times 10^6$/mL in PBS as described in Example 2 above. To 1.35 mL of cell suspension, 85 uL of anti-CD 4 MAb (Gen-Trac, Plymouth Meeting, Pa.) was added at a concentration of 0.1 mg/mL (total 8.5 micrograms MAb) with mixing and incubated five minutes. Next, 1.35 mL GAMFc magnetic colloid was added (67.5 micrograms Fe), mixed, and incubated for five minutes; 2.6 mL of this mixture was immediately placed in a fabricated polystyrene separation vessel (internal dimensions 10 mm × 8 mm ×51 mm high). Finally, this separation vessel cell was placed in a quadrupole device.

The quadrupole was constructed from four bar magnets which were 5.0 cm long, 1.6 cm wide and 1.9 cm deep and they were magnetized through the 1.9 cm dimension. The flux density at the pole faces was 6.6 KGauss and the radius of the quadrupole was 1.1 cm. Thus, the gradient for the device so constructed was 6 KGauss/cm. The 10 × 51 mm face of the separator vessel was placed directly on one of the pole faces, hence separation took place radially through the 8 mm dimension of the vessel.

Magnetic separations were performed for five minutes, ten and fifteen minutes, respectively, on identically prepared samples. All operations were performed at room temperature.

Further, the GAMFc colloid buffer (PBS containing 5% BSA) also included 1% Tamol-850 (Rohm-Haas, Philadelphia, Pa.) to prevent non-specific binding of colloid to cells. Cell supernatant was removed from the separation vessel with a 20 gauge needle placed at the back of the vessel (nearest the center of the quadrupole) and aliquots counted for $Cr^{51}$, and also visually counted on a hemocytometer. For these experiments, it was found that 48, 83 and 90% of the cells were pulled to the surface of the vessel facing the pole piece in 5, 10 and 15 minutes, respectively. In the absence of MAb, or with non-specific MAb no depletion of cells took place. For experiments done in which cells were washed free of excess MAb after MAb incubation, followed by addition of GAMFc colloid, cell depletions over the 5, 10 and 15 minute magnetic separation periods were considerably lower.

It is interesting to note that the amount of MAb left free in solution far exceeds that on cells. If it is assumed that the cell has 50,000 receptors and can bind that many MAbs, then less than 0.05 micrograms of MAb is consumed, or 8.45 micrograms remain in solution. Despite that quantity of MAb in solution and the fact that there is excess colloid in solution, separation is readily accomplished. At the dilution of GAMFc colloid used for cell separation, agglutination reactions between MAb remaining free in solution and excess magnetic capture agent are not visually apparent and, indeed, if small complexes do exist, they are not deleterious to the separation.

The ability to do such separations without removing excess MAb has very beneficial implications for cell analysis, in addition to simplifying procedures. Not only would improved viability of cells be expeted by reducing manipulations, but obviating removal of excess MAb permits the use and exploitation of lower affinity antibodies which, when added in excess, can be "forced" on to receptors, but which readily disassociate when excesses are removed. Additionally, this methodology enables the use of relatively low-affinity, non-antibody receptors including lectins, such as concanavilin A, soybean agglutinin or wheat germ agglutinin for cell labeling via selection of an appropriate common capture magnetic colloid.

From the foregoing experiments, it is clear that a multipole arrangement is useful for separating small magnetic particles from a fluid containing same, e.g., for analytical purposes. Alternatively, a continuous flow system of essentially the same design could be constructed for removing colloidal magnetic material from a moving carried fluid, where such capability is desired in a particular application, such as bioprocessing.

While various aspects of the present invention have been described and exemplified above in terms of certain preferred embodiments, various other embodiments may be apparent to those skilled in the art. For example, the method of the invention may be scaled up to accommodate large volumes of material for various industrial processing applications, especially bioprocessing. The invention is, therefore, not limited to the embodiments specifically described and exemplified, but is capable of variation and modification without departing from the spirit of the invention, the full scope of which is delineated by the appended claims.

What is claimed is:

1. A magnetic separator for separating magnetic particles from a non-magnetic test medium in which said magnetic particles are suspended, the separator comprising:
   (a) a non-magnetic container having a peripheral wall with an internal surface area for receiving said test medium; and
   (b) magnetic means for generating a magnetic field gradient within said container, in which the magnetic field is stronger in the test medium along said internal surface area of said wall than in said test medium most distant from said wall and is operative upon said magnetic particles within said test medium to attract said magnetic particles toward said surface area and cause such particles to be adhered to said area, said magnetic means comprising a plurality of north magnetic poles and a plurality of south magnetic poles positioned alternately around an exterior surface of said peripheral wall of said container and defining a receptacle for said container, said container being removably mounted in said receptacle.

2. A magnetic separator as claimed in claim 1, wherein said magnetic poles are mounted on a cylindrical ferromagnetic yoke disposed around said container, said magnetic poles being intermediate said container and said yoke.

3. A magnetic separator as claimed in claim 2, wherein said magnetic means generates a field of about 5 to about 30 KGauss.

4. A magnetic separator as claimed in claim 1, wherein said magnetic means comprises multiple magnets.

5. A magnetic separator as claimed in claim 4, wherein said container is of cylindrical configuration and each of said magnets has a curved pole face, said faces being disposed in a circle substantially concentric with said container.

6. A magnetic separator as claimed in claim 4, wherein said magnetic means also comprises a magnetic flux concentrating means associated with at least one of said magnets.

7. A magnetic separator as claimed in claim 6, wherein said flux concentrating means is a pole piece.

8. A magnetic separator as claimed in claim 1, wherein said magnetic means comprises at least four magnets surrounding said container with poles of like polarity confronting one another.

9. A magnetic separator as claimed in claim 1, wherein said magnetic means comprises six magnets spaced substantially equidistantly around the periphery of said container.

10. A magnetic separator useful for separating magnetic particles from a non-magnetic test medium in which said particles are suspended, said separator comprising:
   (a) a plurality of non-magnetic containers, having peripheral walls with internal surface area for receiving said test medium;
   (b) a non-magnetic carrier for said plurality of containers, said carrier including a base, said base being generally planar and having an outer edge with means for engaging said containers adjacent to said outer edge of said carrier; and
   (c) magnetic means surrounding said carrier for generating a magnetic field gradient that is operative upon magnetic particles within said test medium in each container to attract said particles toward said internal surface area closest to said magnetic means, thereby causing such particles to be adhered to said surface without substantial entrapment of interfering substances.

11. A magnetic separator as claimed in claim 10, wherein said magnetic means comprises at least four magnets spaced around said carrier, each of said magnets having a face confronting the face of one other magnet, said confronting faces being substantially diametrically opposed and being of the same polarity, said containers being positioned between the confronting magnet faces.

12. A magnetic separator as claimed in claim 11, wherein said magnetic means also comprises a magnetic flux concentrating means associated with each of said four magnets.

13. A magnetic separator as claimed in claim 10, wherein said magnetic means comprises six magnets spaced around said carrier, each of said magnets having a face confronting the face of one other magnet, said confronting faces being substantially diametrically opposed and being of opposite polarity, said containers being positioned between said confronting magnets.

14. A magnetic separator as claimed in claim 13, wherein said magnetic means also comprises a magnetic flux concentrating means associated with each of said six magnets.

15. A magnetic separator useful for separating magnetic particles from a non-magnetic test medium in which said particles are suspended, said separator comprising:

(a) a non-magnetic container having a peripheral wall forming an internal surface area and an inner cross-sectional space inside the container, an inlet port at one end dimensioned to cause the test medium to flow into the inner cross-sectional space, and an outlet port in said container at the end opposite said one end for discharging said non-magnetic test medium; and (b) magnetic means external to said container and capable of applying a magnetic field transverse to said peripheral wall thereby to generate a magnetic field gradient in the test medium within said container, in which the magnetic field is stronger in said test medium along said internal surface area of said wall than in the test medium in a central portion of the cross-sectional space, and operative upon said magnetic particles to attract said particles toward said surface area and cause such particles to be adhered to said area, said magnetic means comprising a plurality of north magnetic poles and a plurality of south magnetic poles positioned alternately around an external surface of said peripheral wall of said container; and (c) said container being removably mounted to said magnetic means to permit removal of said magnetic field and said magnetic field gradient and discharge of said magnetic particles from said internal surface area by gravitational force.

16. The separator as claimed in claim 15 wherein the shape of said cross-sectional space is generally cylindrical.

17. The separator as claimed in claim 15 wherein said magnetic means comprises four magnets spaced around said container with each of said magnets having a face confronting the face of one of the other of said magnets, said faces being of the same polarity, said container being positioned between said confronting faces.

18. A magnetic separator as claimed in claim 15, wherein said container includes at least one baffle spaced between said ends inside said container and transverse to said peripheral wall, said baffle having an upstream surface, a downstream surface and, a central opening to confine flow of test medium primarily through the central portion of said cross-sectional space, said upstream surface being effective to guide magnetic particles contacting said baffle toward said wall.

* * * * *

UNITED STATES PATENT AND TRADEMARK OFFICE
CERTIFICATE OF CORRECTION

PATENT NO. : 5,186,827

DATED : February 16, 1993

INVENTOR(S) : Paul A. Liberti; Brian P. Feeley; Dhanesh I. Gohel

It is certified that error appears in the above-identified patent and that said Letters Patent is hereby corrected as shown below:

On the title page,

In the Abstract, last line, before "medium" insert --test--;

Column 3, line 20, after "Hersh et al.," insert --Clinica Chemica Acta, 63: 69-72 (1975). A similar--;

Column 10, line 32, after "as the" delete "o".

Signed and Sealed this

Twenty-third Day of November, 1993

Attest:

BRUCE LEHMAN

*Attesting Officer*   *Commissioner of Patents and Trademarks*